United States Patent
Golden

(10) Patent No.: US 9,889,089 B2
(45) Date of Patent: *Feb. 13, 2018

(54) DIETARY SUPPLEMENT NON-FLUORIDE TOOTHPASTE AND METHODS OF MAKING AND USING SAME

(71) Applicant: Golden Products LLC, Howard Beach, NY (US)

(72) Inventor: Bruce Alan Golden, Hewlett Harbor, NY (US)

(73) Assignee: Golden Products LLC, Howard Beach, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/090,137

(22) Filed: Apr. 4, 2016

(65) Prior Publication Data

US 2017/0281538 A1  Oct. 5, 2017

(51) Int. Cl.

| | | |
|---|---|---|
| *A61Q 11/00* | (2006.01) | |
| *A61K 8/04* | (2006.01) | |
| *A61K 8/67* | (2006.01) | |
| *A61K 8/06* | (2006.01) | |
| *A61K 9/00* | (2006.01) | |
| *A61K 31/4415* | (2006.01) | |
| *A61K 31/455* | (2006.01) | |
| *A61K 8/34* | (2006.01) | |
| *A61K 8/19* | (2006.01) | |
| *A61K 8/25* | (2006.01) | |
| *A61K 8/92* | (2006.01) | |
| *A61K 8/55* | (2006.01) | |
| *A61K 31/593* | (2006.01) | |
| *A61K 31/355* | (2006.01) | |
| *A61K 8/29* | (2006.01) | |
| *A23L 1/30* | (2006.01) | |
| *A23L 1/302* | (2006.01) | |

(52) U.S. Cl.
CPC ............ *A61K 9/0053* (2013.01); *A23L 1/30* (2013.01); *A23L 1/302* (2013.01); *A23L 1/3006* (2013.01); *A61K 8/19* (2013.01); *A61K 8/25* (2013.01); *A61K 8/29* (2013.01); *A61K 8/345* (2013.01); *A61K 8/553* (2013.01); *A61K 8/922* (2013.01); *A61K 31/355* (2013.01); *A61K 31/4415* (2013.01); *A61K 31/455* (2013.01); *A61K 31/593* (2013.01); *A61Q 11/00* (2013.01); *A23V 2002/00* (2013.01); *A61K 2800/28* (2013.01); *A61K 2800/49* (2013.01); *A61K 2800/591* (2013.01); *A61K 2800/74* (2013.01); *A61K 2800/805* (2013.01)

(58) Field of Classification Search
CPC . A61Q 11/00; A61K 2800/92; A61K 2800/48
See application file for complete search history.

(56) References Cited

U.S. PATENT DOCUMENTS

| | | | |
|---|---|---|---|
| 3,929,987 A | 12/1975 | Colodney et al. | |
| 3,943,240 A | 3/1976 | Delaney et al. | |
| 3,991,177 A | 11/1976 | Vidra et al. | |
| 4,123,517 A | 10/1978 | Baines et al. | |
| 4,603,045 A | 7/1986 | Smigel | |
| 5,531,982 A | 7/1996 | Gaffar et al. | |
| 5,624,906 A | 4/1997 | Vermeer | |
| 6,042,812 A * | 3/2000 | Sanker | A61K 8/21 424/49 |
| 6,117,415 A * | 9/2000 | Schwarz | A61K 8/062 424/49 |
| 9,066,889 B2 | 6/2015 | Golden | |
| 9,114,097 B1 * | 8/2015 | Aminpour | A61K 8/97 |
| 2001/0044475 A1 | 11/2001 | Matsuzaki et al. | |
| 2002/0048553 A1 | 4/2002 | Baumgartner | |
| 2003/0152524 A1 | 8/2003 | Eshita | |
| 2003/0170185 A1 | 9/2003 | Takatsuka et al. | |
| 2003/0180229 A1 | 9/2003 | Kosti | |
| 2005/0152851 A1 | 7/2005 | Kaminski | |
| 2006/0057213 A1 | 3/2006 | Larhrib et al. | |
| 2006/0142351 A1 | 6/2006 | Murray | |
| 2009/0117058 A1 * | 5/2009 | Lee | A61Q 11/00 424/53 |

(Continued)

FOREIGN PATENT DOCUMENTS

| | | |
|---|---|---|
| KR | 2005058069 A | 6/2005 |
| KR | 10-0564231 B1 | 3/2006 |
| WO | WO 2014160285 A1 * | 10/2014 ............ A61K 35/37 |

OTHER PUBLICATIONS

CFTA International Cosmetic Ingredient Dictionary, 4th Edition, published by The Cosmetic, Toiletry, and Fragrance Association. Washington D.C.
Drugs.com, Pantothenic Acid (Systemic), http://web.archive.org/web/20080726171547/http://www.drugs.com/mmx/calcium-pantothenate.html, pp. 1-8, Jul. 2008.
MEDLINEplus, Toothpaste Overdose, Jun. 17, 2001, pp. 1-2.
Delta Dental, Brush and floss regularly for good oral health, Jul. 7, 2007, pp. 1-2.
Physicians Desk Reference (PDR 54 ED 2000), pp. 551-552.
Drugs.com, Vancomycin Hydrochloride, Jun. 12, 2012, pp. 1-2.
Boots WebMD, Jun. 12, 2012, Chlorhexidine, pp. 1-2.

*Primary Examiner* — Tracy Liu
(74) *Attorney, Agent, or Firm* — Dilworth & Barrese, LLP

(57) ABSTRACT

Provided herein is a storage stable non-fluoride toothpaste composition enriched with a dietary supplement containing both oil soluble and water soluble vitamins. The dietary supplement is incorporated into the toothpaste, the dietary supplement containing a water soluble vitamin portion including at least one water soluble vitamin and an oil soluble vitamin portion. The oil soluble vitamin portion includes at least one oil soluble vitamin, a carrier oil and an emulsifier. The toothpaste is thereby formulated in a manner such that oral application will result in systemic delivery of at least a portion of the dietary supplement to meet a 2% RDI threshold even when 3 or less serving sizes are orally applied.

25 Claims, No Drawings

(56) References Cited

U.S. PATENT DOCUMENTS

| | | | |
|---|---|---|---|
| 2010/0297197 A1* | 11/2010 | Golden | A61K 8/19 424/401 |
| 2011/0117175 A1* | 5/2011 | Rosenbaum | A61K 9/006 424/443 |
| 2012/0082628 A1* | 4/2012 | Haught | A61Q 11/00 424/51 |
| 2014/0287046 A1 | 9/2014 | Golden | |

* cited by examiner

DIETARY SUPPLEMENT NON-FLUORIDE TOOTHPASTE AND METHODS OF MAKING AND USING SAME

BACKGROUND

Technical Field

The present disclosure relates generally to oral hygiene products and more particularly to a toothpaste which contains a dietary supplement.

Background of the Art

Oral hygiene products, such as toothpaste, are commonly used in the treatment and prophylaxis of oral disease or tooth decay. Many oral diseases or tooth decay are associated with the buildup of plaque in the oral cavity and particularly around the teeth. Plaque is a soft and gel-like film having a high concentration of bacteria. Bacterial plaque can use the sugars in food to produce acids which eat away at the tooth enamel to produce a cavity. If the plaque isn't removed it eventually forms a hardened layer of calculus (tartar) which makes brushing and flossing more difficult. As plaque and calculus continue to build up the gum tissue becomes swollen and inflamed leading to gum diseases such as gingivitis and periodontal disease. Gingivitis, periodontal disease and other associated oral diseases can be treated with professional help, flossing and brushing with toothpaste.

Fluoride compounds are typically added to toothpaste to reduce tooth decay. Both children and adults benefit from fluorides. For example, fluoride incorporates itself into the tooth enamel to make the teeth more resistant to acids. The topical application of fluorides in toothpastes to the surface of the teeth promotes remineralization of the tooth enamel and helps to inhibit or reverse tooth decay. Typical fluorides for use in toothpaste include sodium monofluorophosphate, stannous fluoride, and sodium fluoride.

However, fluoride is a known toxin. It has been associated with thyroid problems, osteoporosis, endocrine problems and cancers. More commonly, it has been found to cause dental and skeletal fluorosis, most commonly in young children. Skeletal fluorosis can affect the neurodevelopment of children. The Food and Drug Administration (FDA) classifies fluoride toothpastes as drugs. Consumers are advised not to swallow a fluoride toothpaste and to seek professional help or contact a poison control center if they do. Clearly, fluoride toothpastes are not intended to be ingested. Special care must be taken with children under 6 years of age since their swallowing reflexes are not yet fully developed and are likely to swallow rather than spit out toothpaste or mouthwash.

Toothpastes generally include an abrasive material dispersed in a gel or paste. Abrasives remove stains and plaque, as well as polish the teeth. Common abrasives include calcium phosphate, alumina, calcium carbonate and silica. The toothpaste should be sufficiently abrasive to polish the teeth, but without damaging the tooth enamel.

A toothpaste containing a dietary supplement has been recently formulated. Such a toothpaste and method of use has been described in U.S. Pat. No. 9,066,899, the entire disclosure of which is herein incorporated by reference. Any toothpaste containing a dietary supplement and which is intended to be ingested must exclude fluorides and any non-food ingredients as per the FDA.

Dietary supplements are used widely to supplement the body's production or lack of production of certain essential elements. For example, over 50% of all Americans take dietary supplements on occasion. Common supplements include vitamins, minerals and botanicals. However, many of these dietary supplements are individually sold. For example, various vitamins are generally sold separately so a consumer will have to purchase vitamin A separate from vitamin B and so forth. This can be time consuming, but more importantly, this can become tedious when it is time to administer these various dietary supplements. Busy schedules often time do not permit the time for consumers to intake these supplements daily.

The term "dietary supplement" was defined in the Dietary Supplement Health and Education Act (DSHEA) of 1994. In short, a dietary supplement is a product taken orally that contains a dietary ingredient intended to supplement the diet. The dietary ingredients may include, for example, one or more of vitamins, minerals, herbs or other botanicals, amino acids, enzymes, organ tissues, glandulars and metabolites. Dietary supplements can also be extracts or concentrates, and may be found in such forms as tablets, capsules, soft gels, gel caps, liquids and powders. The DSHEA classifies dietary supplements as foods, not drugs and are meant to be ingested. If a product contains less than 2 percent of the reference daily intake (RDI) of a given dietary supplement, that product is not considered to be a "significant source" of that dietary supplement. The term "reference daily intake" (RDI) shall be understood herein to refer to the estimated daily intake values for vitamins, minerals, and other dietary ingredients established by the FDA. For example, the RDI for vitamin B1 is about 1.1 mg; the RDI for vitamin B6 is about 2.0 mg; the RDI for vitamin A is about 5,000 International Units (IU); the RDI for vitamin D3 is about 400 IU; the RDI for vitamin E is about 30 IU; the RDI for niacinamide is about 18 mg; the RDI for vitamin B12 is about 6 micrograms (pig); the RDI for D-calcium pantothenate is about 10.0 mg; the RDI for sodium selenate is about 70 µg; the RDI for zinc lactate is about 15 mg; the RDI for magnesium sulfate is about 400 mg; and the RDI for sea salt is about 2300 mg.

The non-fluoride daily supplement-containing toothpaste of U.S. Pat. No. 9,066,889 contains at least 2% of the RDI of the dietary supplement in a serving size amount when ingested as indicated therein. What has been achieved herein is a stable formulation containing a much higher percentage of the dietary supplement RDI in a non-fluoride, non-drug containing toothpaste.

SUMMARY

Provided herein is a non-fluoride containing dietary supplement enriched toothpaste suitable for ingestion, the toothpaste comprising (a) a dentally acceptable oral vehicle having a pasty consistency; and (b) a dietary supplement containing a water soluble vitamin portion including at least one water soluble vitamin and an oil soluble vitamin portion, said oil soluble vitamin portion including at least one oil soluble vitamin, a carrier oil and an emulsifier, wherein a serving size amount of the toothpaste contains at least 2% of a reference daily intake (RDI) of each vitamin in said dietary supplement. Also provided herein are methods for making and using the toothpaste. It has been surprisingly found herein that a toothpaste formulation that is suitable for children as well as adults and which contains a sufficient amount of dietary supplements such that oral application of the toothpaste will result in systemic delivery of the dietary supplement. Moreover, the toothpaste of the present invention comprises a stable formulation including both oil soluble and water soluble vitamins with minimal degradation over time.

DETAILED DESCRIPTION OF PREFERRED EMBODIMENT(S)

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

Other than in the working examples or where otherwise indicated, all numbers expressing amounts of materials, reaction conditions, time durations, quantified properties of materials, and so forth, stated in the specification and claims are to be understood as being modified in all instances by the term "about."

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The non-fluoride toothpaste of the present invention includes a dietary supplement carried in an oral vehicle and is suitable for ingestion by both children and adults. In a serving size amount, the toothpaste includes at least 2% of the RDI of the dietary supplement, preferably more than 2% of the RDI of the dietary supplement and up to about 150% or more of the RDI of the dietary supplement, preferably at least about 10% to 80% of the RDI, and more preferably at least about 50% to 80% of the RDI of the dietary supplement in said serving size amount of the toothpaste. The serving size amount is a quantity of toothpaste of from about 0.5 grams to about 3 grams, and preferably from about 1.0 gram to about 1.5 grams. The serving size amount is contained in about a ¾ inch to 1 inch strip of toothpaste as applied to a conventional toothbrush from a conventional toothpaste tube. The toothpaste can be deliberately ingested. However, an adult user generally swallows about 10% to 30% of the toothpaste naturally while brushing the teeth. Children can swallow up to 100% of the toothpaste. A user who brushes multiple times a day with the non-fluoride containing dietary supplement toothpaste of the present invention, for example two to three times per day or more, can naturally receive at least the 2% minimum of the RDI to provide a significant amount of the dietary supplement, preferably at least about 10%-80 of the RDI, more preferably at least about 50%-80% of the RDI, and even more preferably up to about 150% or more of the RDI. Deliberate ingestion of the toothpaste increases the amount of dietary supplement received.

In order to make the dietary supplement toothpaste described herein, the ingredients are combined in accordance with a protocol as set forth below. The toothpaste ingredients are all food grade and "generally recognized as safe" (GRAS) and are safe to swallow. The toothpaste includes both water soluble vitamins (B vitamins) and oil soluble vitamins (e.g., vitamins D and E). In order to obtain a stable higher loading of the oil soluble vitamins these vitamins are carried in an oil and emulsifier in the toothpaste. The steps of the mixing protocol described below provide a desired stability. By "stability" or "stable formulation" is meant that there are no significant physical changes in the toothpaste after six months to two years of storage of the toothpaste under room temperature conditions (i.e., 25° C. and 60% relative humidity) as would be found in a typical home, and also at elevated temperatures (i.e., 40° C. and 75% relative humidity) for six months. That is, the toothpaste is color stable and odor stable. The pH of the toothpaste remains at between 6.0-8.0, preferably 6.5-7.5, and the viscosity remains at between 200,000-400,000 cps, preferably 300,000-350,000 cps.

In an embodiment the toothpaste of the present invention includes a water based oral vehicle and a dietary supplement as follows.

Oral Vehicle Components

The oral vehicle of the toothpaste includes a thickening agent that imparts a pasty consistency and provides body and texture to the paste. The thickening agent facilitates the application of the toothpaste to a toothbrush or other tooth cleaning device. Some exemplary materials which are suitable for inclusion in the dentifrice paste to apply texture or pasty consistency to the toothpaste include gums, such as cellulose gum, xantham gum, carrageenan, guar gum, locust bean gum or similar materials and compositions. Gum base may be prepared by, for example, dissolving carboxymethylcellulose (CMC) in hot water, adding xantham gum, and mixing to uniformity. The gum base also serves as an emulsifier. A thickening agent suitable for use in the invention is a carboxymethyl cellulose available under the designation AQUALON®9H4F cellulose gum available from Ashland Inc. of Covington Ky. Calcium carbonate also functions as a thickening agent.

In order to prevent the toothpaste from drying out, a humectant is preferably included in the composition. Suitable humectants include glycerin and sorbitol. Glycerin also acts as a natural preservative. Sorbitol also acts as a sweetener and an anticavity agent.

Commonly available sweeteners which may be included as ingredients in the formulation of the present invention include, for example, stevia (truvia rebiana), xylitol and monoammonium glycyrrhizinate, as well as sorbitol. Other sweeteners which may be used include saccharine, cyclamate, aspertame, and the like. Xylitol also functions as an anticavity agent.

The toothpaste preferably also includes flavorants such as peppermint, wintergreen, cinnamon or clove. Many other flavorants are known in the art. A preferred flavorant is bubble gum flavor.

The toothpaste also includes mild abrasives such as calcium carbonate and/or silica (e.g., ZEODENT® 113 or 165). Titanium dioxide ($TiO_2$) serves as a colorant to whiten the toothpaste. No dyes are included in the formulation.

The oral vehicle can also include a chelating agent such as glucono delta lactone, which binds heavy metal ions.

The above listed components of the oral vehicle are combined in water.

Dietary Supplement Components

Various dietary supplements are contemplated for inclusion in the instant toothpaste. Suitable and exemplary dietary supplements include vitamins such as vitamin A, vitamin B-1, vitamin B-6, vitamin C, vitamin D-3, vitamin E, niacin, vitamin B-12, pantothenate and mixtures thereof. Vitamin D can be present as cholecalciferol, vitamin E as tocopherol E acetate, niacin as niacinamide; vitamin B6 as pyridoxine HCl; pantothenate as pantothenic acid or calcium pantothenate. Vitamins A, D and E are oil soluble vitamins. Vitamins C and the B vitamins are water soluble.

Also, mineral dietary supplements may be included in the toothpaste of the invention such as calcium carbonate as well as zinc, selenium, magnesium and manganese as, for example, zinc lactate, sodium selenate, magnesium sulfate and manganese chloride.

The dietary supplement contains a water soluble vitamin portion including at least one water soluble vitamin and an oil soluble vitamin portion. The oil soluble vitamin portion includes at least one oil soluble vitamin, a carrier oil and an emulsifier (i.e., emulsifying agent). The method of the present invention as set forth below includes a method for uniformly dispersing the oil soluble vitamins in the water based oral vehicle. The dietary supplement formulation includes a carrier, such as coconut oil or other food grade oil, such as corn oil, soy bean oil, safflower oil, sunflower oil, cannola oil, olive oil and the like. The preferred carrier oil for use in the present invention is coconut oil, which contains a number of saturated fatty acids such as caprylic acid, decanoic acid, lauric acid, myristic acid, palmitic acid, oleic acid, and other fatty acids. The emulsifier is a food grade emulsifier such as glycerol fatty acid esters, sucrose fatty acid esters, sorbitan fatty acid esters, propylene glycol fatty acid esters, polysorbate, and lecithin. Typical examples of the glycerol fatty acid esters include polyglycerin esters, monoglycerides, organic acid monoglycerides, and diglycerin monofatty acid esters. A preferred emulsifier for use in the present invention is soy lecithin. It is believed that globules of the carrier oil (e.g., coconut oil) form with the oil soluble vitamins (e.g., vitamins D and E). The emulsifier (e.g., soy lecitin) orients itself in such a way that the oil soluble portion of the lecitin molecule dissolves in the oil and the water soluble portion of the lecithin molecule dissolves in the water so that it forms a barrier coating around the oil globule. This coating protects the oil soluble vitamins in the carrier oil from breakdown to provide stability and more consistent RDI over time.

In an exemplary embodiment the toothpaste of the present invention includes the following ranges of composition for the various ingredients:

Based on total composition weight, in an embodiment the toothpaste can comprise, for example, 0.5-1.5 wt % thickening agent, 8-20 wt % sweetener, 10-25 wt % humectant, 30-40 wt % abrasive/whitener, 0.25-1.0 wt % flavorant, 15-20 wt % water, 3.5-4.5 wt % vitamins, 0.5-1.5 wt % carrier oil and 0.05-2.0 wt % emulsifier.

More particularly, an exemplary embodiment of the toothpaste of the invention can include the following composition ranges of ingredients in the formulation, although composition percentages outside the ranges listed below may be employed when suitable for the purposes described herein:

| Ingredients | Composition ranges (w % based on total composition weight) |
|---|---|
| Oral Vehicle | |
| Water | 15-20 |
| Thickener | |
| Carboxymethyl cellulose gum (CMC)* | 0.5-1.5 |
| Calcium carbonate** | 30-40 |
| Abrasive/whitener | |
| Titanium dioxide | 0.5-1.5 |
| Silica | 1-3 |
| Humectant | |
| Glycerin | 1-10 |
| Sorbitol | 5.0-10 |
| Sweetener | |
| Stevia | 0.5-1.5 |
| Xylitol | 5.0-15 |
| Monoammonium glycyrrhizinate | 0.01-0.10 |
| Chelating agent | |
| Glucono delta lactone | 0.05-0.15 |
| Flavorant | 0.5-1.0 |
| Dietary Supplement | |
| Vitamin B6 (Pyridoxine hydrochloride) | 0.05-0.15 |
| Niacinamide | 0.5-1.5 |
| Calcium pantothenate | 0.2-0.7 |
| Vitamin E, (Tocopherol acetate) | 1.0-2.0 |
| Vitamin D-3, (cholecalciferol in oil, 1 million units per gram) | 0.01-0.05 |
| Soy lecithin (emulsifier) | 0.05-0.50 |
| Coconut oil (carrier oil for oil soluble vitamins) | 0.5-1.5 |

*CMC also serves as an emulsifier
**Calcium carbonate also serves as a mineral supplement A method for making the toothpaste of the invention generally comprises separately combining the oil soluble vitamin with the carrier oil and emulsifier in a first container, combining glycerin, thickener and titanium dioxide whitener in a separate second container, and combining water, humectant, sweetener, abrasive, chelating agent and water soluble vitamins in a separate third container, combining the contents of the first container with those of the third container, then combining the contents of the second container with the combined contents of the first and third containers.

More particularly, in a preferred method for preparing the toothpaste of the present invention the following procedure is performed:

Coconut oil and granular soy lecithin are combined in a first container and heated with agitation to a temperature of 65° C.-70° C. and mixed until all solids are brought into solution. The temperature is maintained with fast mixing until a clear, uniformly brown oil is produced. Thereafter, the solution is allowed to cool to 25° C.-30° C.

Then, Vitamin E acetate and Vitamin D-3 are added with agitation.

In a second container glycerin and cellulose gum are combined with agitation until a uniform slurry is produced. Then water dispersible titanium dioxide is added to the slurry until fully and uniformly dispersed. Mixing is maintained to prevent the titanium dioxide from settling out.

In a third container the following components are added one at a time preferably in the following order, mixing until each powder dissolves fully between additions, and recirculating while adjusting mixing speeds when necessary:

Purified water
Glucono delta lactone
Xylitol
Truvia rebiana
Pyridoxine HCl
Niacinamide
Calcium pantothenate
Monoammonium glycyrrhizinate
Glycerin
Sorbitol When all of the powders are uniformly dissolved the agitation is reduced to a slow speed and Calcium carbonate and silica are added one at a time with care to avoid air entrapment.

When the combined ingredients of the third container are mixed to uniformity, the premixed components of the first container (coconut oil with soy lecithin and the oil soluble vitamins) are added to the components of the third container with slow mixing, to avoid air entrapment until a uniform, lump free paste is obtained.

Thereafter, the premixed components of the second container (glycerin, cellulose gum and titanium dioxide) are added to the third container with slow mixing to avoid air entrapment until a uniform, lump free paste is obtained.

Finally, the flavorant is added to the combined ingredients with slow mixing until the desired toothpaste is obtained.

In use, a serving size amount of the toothpaste of the present invention (as defined above) is applied to the teeth of a mammal (for example, a human), either on a toothbrush or directly. The applied toothpaste is then used to clean and/or polish the teeth of the mammal. In doing so, at least a portion of the toothpaste, which contains the dietary supplement, is ingested by the mammal and supplements the diet of the mammal. This method can be repeated multiple times in a 24-hour period and preferably is repeated at least two to three times in a 24-hour period.

EXAMPLE

A suitable toothpaste in accordance with the present invention was prepared as follows. All ingredients are generally recognized as safe and are food grade. The vitamin content of the toothpaste of this Example equals at least 25%-75% of the RDI of each vitamin in the dietary supplement in 1.5 grams of toothpaste. In order to ensure that the vitamin content of the packaged toothpaste contains at least 25%-75% of the RDI of the dietary supplement the vitamin content as formulated is equal to the label claim plus 20% excess, except for cholecalciferol, which exceeds the label claim by 35%. The stability of the toothpaste is such that the RDI of each vitamin of the dietary supplement is maintained at 25%-75% after at least six months storage at room temperature conditions. The ingredients are combined as according to the procedure set forth below wherein AQUALON® 9H4F is food grade carboxymethyl cellulose gum (available from Ashland Inc. of Covington Ky.), VICALITY ALBAGLOS® PCC is precipitated calcium carbonate (available from Specialty minerals Inc., of Adams, Mass.), MAGNASWEET® MM100 is a sweetener based on monoammonium glycyrrhizinate (available from Mafco Worldwide LLC of Camden, N.J.), and NAT Bubble Gum FL#10027 is a flavoring agent (available from Virginia Dare of Brooklyn, N.Y.). Percentage composition is based on the total weight of the formulation.

Formulation

| INGREDIENTS | PERCENTAGE COMPOSITION |
|---|---|
| PHASE A (Main Phase) | |
| Water (Purified deionized) | 18.9 |
| Glucono delta lactone, (fine gran. USP FCC) | 0.10 |
| Xylitol | 10.00 |
| Truvia rebiana (stevia extract) | 0.80 |
| Pyridoxine HCl (USP) | 0.10 |
| Niacinamide (USP) | 1.00 |
| Calcium pantothenate (natural) | 0.55 |
| MAGNASWEET ® MM100 | 0.08 |
| Glycerin (USP) | 16.40 |
| Sorbitol (70% USP FCC) | 8.00 |
| VICALITY ALBAGLOS ® PCC (CaCO$_3$) | 32.00 |
| ZEODENT ® 113 silica | 8.00 |
| NAT Bubble gum #10027 MN82 | 0.80 |
| PHASE B (Premix) | |
| Coconut Oil | 1.00 |
| Soy lethicin | 0.10 |
| Tocopherol acetate (Vitamin E, synthetic) | 1.50 |
| Cholecalciferol (in corn oil, 1 million units per g., Vitamin D-3) | 0.02 |
| PHASE C (Premix) | |
| Glycerin 99% (ISP) | 5.00 |
| AQUALON ® 9H4F cellulose gum | 0.65 |
| Titanium dioxide (USP BC, water dispersible) | 1.00 |
| Total | 100.00 |

The formulation described above was mixed in accordance with the following steps:

1. Preparation of Premix PHASE B Oil Soluble Vitamin Phase:

In a separate sanitized container the coconut oil and soy lecithin were combined with agitation and heated to about 65° C. to about 70° C. and mixed with agitation until all solids were hydrated into solution until a uniform brownish oil was produced. The brownish oil was then allowed to cool to about 25° C. to about 30° C. and the tocopherol acetate (synthetic Vitamin E) and cholecalciferol in corn oil (Vitamin D-3) were added one at a time with agitation until a uniform PHASE B was achieved.

2. Preparation of Premix PHASE C Gum Phase

In a separate sanitized container the glycerin and AQUALON® 9H4F cellulose gum were combined with agitation and mixed to form a uniform smooth slurry without lumps. Then titanium dioxide was added to the slurry with continuous agitation until uniformly dispersed in a PHASE C gum phase. The agitation was maintained to prevent the titanium dioxide from settling out while preparing the main PHASE A. Steps 1 and 2 may optionally be performed in reverse order or simultaneously.

3. Preparation of Main PHASE a Water Soluble Vitamin Phase.

In a separate sanitized container with prop agitation the following components were added one at a time in the following order, and mixed until each powder dissolved fully between additions, and recirculated with adjustment of the mixing speed to maintain uniformity: purified water, glucono delta lactone, xylitol, truvia rebiana, pyridoxine HCl, niacinamide, calcium pantothenate, monoammonium glycyrrhizinate, glycerin, and sorbitol. Samples were taken periodically and examined to insure uniformity. Then the VICALITY ALBAGLOS® calcium carbonate and ZEODENT® 113 silica were added one at a time with agitation slowed sufficiently to prevent air entrapment into the mixture. Mixing was continued for at least two hours to provide a creamy, lump free PHASE A paste.

4. Combination of Premix PHASE B and Main PHASE A.

The completed and uniform premix PHASE B oil soluble vitamin phase was then added to main PHASE A paste with continuous slow mixing for 20-30 minutes to avoid air entrapment until a completely smooth and uniform lump free combined PHASE A/PHASE B paste was achieved.

5. Combination of Premix PHASE C Gum Phase to the Combined PHASE A/PHASE B paste.

The premix PHASE C gum phase was then added to the combined PHASE A/PHASE B mixture with continuous slow mixing for 1-2 hours to avoid air entrapment until a completely smooth and uniform lump free combined PHASE A/PHASE B/PHASE C paste was achieved.

6. Addition of the Flavorant.

The NAT bubble gum flavorant was then added to the combined PHASE A/PHASE B/PHASE C paste with slow mixing for 15-20 minutes to avoid air entrapment to provide a completely smooth and uniform toothpaste in accordance with the present invention.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A method for delivering at least one dietary supplement to a mammal comprising:
   A) brushing the teeth of a mammal multiple times in a 24 hour period with a serving size amount of a non-fluoride, dietary supplement enriched toothpaste suitable for ingestion said toothpaste comprising:
      1) a dentally acceptable oral vehicle having a pasty consistency;
      2) an oil phase containing a carrier oil, an emulsifier and a dietary supplement comprising at least one oil soluble vitamin; and
      3) an aqueous phase containing water and a dietary supplement comprising at least one water soluble vitamin; and
   B) ingesting at least a portion of said serving size amount of said toothpaste during each brushing,
   and wherein said serving size amount of said toothpaste is formulated so that after said brushing multiple times and said ingesting, at least 2 percent of the reference daily intake (RDI) of the dietary supplement is provided to said mammal.

2. The method of claim 1 wherein said steps (A) and (B) are performed at least three times in a 24 hour period.

3. The method of claim 1 wherein the serving size amount comprises from about 1.0 to about 3.0 grams.

4. The method of claim 1 wherein at least about 10% to about 150% of the RDI of the dietary supplement is provided to said mammal.

5. The method of claim 1 wherein at least about 50% to about 150% of the RDI of the dietary supplement is provided to said mammal.

6. The method of claim 1 wherein the serving size amount contains at least 2% of the RDI of each vitamin in the toothpaste.

7. The method of claim 1 wherein the serving size amount contains at least about 10% to 80% of the RDI of each vitamin in the toothpaste.

8. The method of claim 1 wherein the serving size amount contains at least about 50% of the RDI of each vitamin in the toothpaste.

9. The method of claim 1 wherein the serving size amount contains at least about 80% of the RDI of each vitamin in the toothpaste.

10. The method of claim 1 wherein the serving size amount comprises from about 0.5 to about 3.0 grams.

11. The method of claim 1 wherein the serving size amount comprises from about 1.0 to about 1.5 grams.

12. The method of claim 1 wherein the serving size amount comprises about a ¾ inch to 1 inch strip of toothpaste applied to a toothbrush.

13. The method of claim 1 wherein the oil soluble vitamin is at least one vitamin selected from the group consisting of Vitamin D-3 and Vitamin E.

14. The method of claim 1 wherein the carrier oil is selected from the group consisting of corn oil, soy bean oil, safflower oil, sunflower oil, cannola oil, olive oil and coconut oil.

15. The method of claim 1 wherein the carrier oil is coconut oil.

16. The method of claim 15 wherein the at least one oil soluble vitamin comprises vitamin D-3 and vitamin E.

17. The method of claim 1 wherein the emulsifier is selected from the group consisting of glycerol fatty acid esters, sucrose fatty acid esters, sorbitan fatty acid esters, propylene glycol fatty acid esters, polysorbate, lecithin and combinations thereof.

18. The method of claim 1 wherein the emulsifier is soy lecithin.

19. The method of claim 1 wherein the water soluble vitamin comprises at least one vitamin selected from the group consisting of Vitamin B-1, Vitamin B-6, Vitamin C, niacin, Vitamin B-12, and pantothenate.

20. The method of claim 1 wherein said toothpaste further comprises glucono delta lactone, glycerin, xylitol, monoammonium glycyrrhizinate, sorbitol, cellulose gum, sweetener, whitener and flavorant.

21. The method of claim 1, wherein said toothpaste further comprises:
   a thickener selected from the group consisting of cellulose gum, xantham gum, carrageenan, guar gum, locust bean gum, calcium carbonate and combinations thereof,
   an abrasive selected from the group consisting of calcium carbonate, silica and combinations thereof,
   a titanium dioxide whitener,
   a humectant selected from the group consisting of glycerin, sorbitol and combinations thereof,
   a sweetener selected from the group consisting of stevia, xylitol, monoammonium glycyrrhizinate and combinations thereof,
   a chelating agent including glucono delta lactone, and
   a flavorant selected from the group consisting of peppermint, cinnamon, clove, wintergreen, bubble gum and combinations thereof.

22. A method for making the toothpaste of claim 21 comprising the steps:
   a) combining the at least one oil soluble vitamin with the carrier oil and emulsifier in a first container to provide the oil phase;
   b) combining glycerin, thickener and titanium dioxide whitener in a separate second container, c) combining the water, humectant, sweetener, abrasive, chelating agent and at least one water soluble vitamin in a separate third container to provide the aqueous phase, d) combining the oil phase and the aqueous phase in such a manner as to form a uniform, smooth paste, then e) combining the contents of the second container with the paste obtained in step d) to provide the non-fluoride, dietary supplement enriched toothpaste.

23. The method of claim 22 wherein the carrier oil is coconut oil, the emulsifier is soy lecithin, and the thickener is cellulose gum, and the method optionally further comprises adding a flavorant to the combined contents of the first, second and third container.

24. The method of claim 23 wherein step (a) comprises combining the coconut oil and soy lecithin and heating same to a temperature of from about 65° C. to about 70° C. with agitation to form a uniform brownish oil, allowing said brownish oil to cool to a temperature of from about 25° C. to about 30° C., then sequentially adding Vitamin E and Vitamin D-3 with agitation to the brownish oil to provide an oil phase;

the step (b) comprises combining glycerin and the cellulose gum with agitation to provide a uniform slurry, then adding the titanium dioxide whitener to the slurry with continuous agitation to provide a premix thickener composition;

step (c) comprises sequentially combining with water the following components: glucono delta lactone, xylitol, stevia, pyridoxine HCl, niacinamide, calcium pantothenate, monoammonium glycyrrhizinate, glycerin, and sorbitol, then adding calcium carbonate and silica with slow agitation to avoid air entrapment to provide an aqueous phase;

step (d) comprises combining the oil phase with the aqueous phase with agitation sufficiently slow to avoid air entrapment to provide a uniform, smooth paste; and step (e) comprises combining the premix thickener composition with the uniform smooth paste to provide the non-fluoride, dietary supplement enriched toothpaste.

25. The method of claim 1, wherein said toothpaste further comprises:
a thickener,
an abrasive,
a titanium dioxide whitener,
a humectant selected from the group consisting of glycerin, sorbitol and combinations thereof,
a sweetener,
a chelating agent, and
a flavorant;
wherein the toothpaste is prepared by i) combining the at least one oil soluble vitamin with the carrier oil and emulsifier in a first container to provide the oil phase;

ii) combining glycerin, thickener and titanium dioxide whitener in a separate second container, and iii) combining water, humectant, sweetener, abrasive, chelating agent and water soluble vitamins in a separate third container to provide the aqueous phase, iv) combining the oil phase with the aqueous phase in such a manner as to form a uniform, smooth paste, then v) combining the contents of the second container with the paste obtain in step iv) to provide the non-fluoride, dietary supplement enriched toothpaste.

* * * * *